US012635960B2

(12) United States Patent
Knowland et al.

(10) Patent No.: US 12,635,960 B2
(45) Date of Patent: May 26, 2026

(54) IN VIVO MEASUREMENT SYSTEM AND METHOD FOR THE LOCALIZED MEASUREMENT OF RADIOTRACER CONCENTRATION IN THE BODY

(71) Applicant: Lucerno Dynamics, LLC, Cary, NC (US)

(72) Inventors: Joshua G. Knowland, Cary, NC (US); Ronald K. Lattanze, Morrisville, NC (US); Paul David Mozley, Collegeville, PA (US); Steven Perrin, Durham, NC (US)

(73) Assignee: Lucerno Dynamics, LLC, Cary, NC (US)

( * ) Notice: Subject to any disclaimer, the term of this patent is extended or adjusted under 35 U.S.C. 154(b) by 0 days.

(21) Appl. No.: 18/598,188

(22) Filed: Mar. 7, 2024

(65) Prior Publication Data

US 2024/0206830 A1     Jun. 27, 2024

Related U.S. Application Data

(63) Continuation of application No. 17/326,445, filed on May 21, 2021, now Pat. No. 11,963,808.

(51) Int. Cl.
A61B 6/00          (2024.01)
A61B 6/40          (2024.01)
(Continued)

(52) U.S. Cl.
CPC ............ A61B 6/4057 (2013.01); A61B 6/425 (2013.01); A61B 6/4258 (2013.01); (Continued)

(58) Field of Classification Search
CPC ...... A61B 6/4057; A61B 6/425; A61B 6/4258
See application file for complete search history.

(56) References Cited

U.S. PATENT DOCUMENTS 3,669,095 A * 6/1972 Kobayashi .............. G01T 1/244
                                                      174/106 SC
3,863,623 A * 2/1975 Trueblood ........... A61B 6/4057
                                                      600/431
(Continued)

OTHER PUBLICATIONS

Warnock, et al., Use of a beta microprobe system to measure arterial input function in PET via an ateriovenous shunt in rats, EJNMMI Research 2011, 1 :13, http://www.ejnmmires.com/content/1 /1 /13.
(Continued)

*Primary Examiner* — Colin T. Sakamoto
(74) *Attorney, Agent, or Firm* — Williams Mullen; R. Brian Drozd

(57)                    ABSTRACT
Various embodiments of a device for in-vivo measurements radiopharmaceuticals used for diagnosis and monitoring of radiotherapy are presented. In some embodiments, the present disclosure relates to a device having a cannula that may include a measurement chamber, a radiation detector and a delivery lumen, wherein the device may be used to both deliver material to the patient (e.g., radiotracers used in radiopharmaceuticals) and measure levels and concentrations of radioactive material in, for example, the patient's blood both during and after administration of the radioactive material. In some embodiments, a plunger may be utilized to draw blood through a first opening into the measurement chamber and then return it to the bloodstream. In some embodiments, particle absorbing materials may be used to limit measurements to materials within the measurement chamber or other area of interest.

19 Claims, 15 Drawing Sheets

(51) Int. Cl.
    *A61B 6/42* (2024.01)
    *A61B 6/50* (2024.01)
(52) U.S. Cl.
    CPC .............. *A61B 6/4429* (2013.01); *A61B 6/48*
                  (2013.01); *A61B 6/50* (2013.01)

(56) References Cited

U.S. PATENT DOCUMENTS

| | | | | |
|---|---|---|---|---|
| 5,008,546 | A * | 4/1991 | Mazziotta | G01T 1/169 |
| | | | | 250/366 |
| 6,076,009 | A * | 6/2000 | Raylman | A61B 6/425 |
| | | | | 250/303 |
| 7,011,814 | B2 | 3/2006 | Suddarth | |
| 9,592,018 | B2 * | 3/2017 | Robertson | A61B 6/4258 |
| 10,524,864 | B2 * | 1/2020 | Sinusas | A61B 18/1492 |
| 2002/0168317 | A1 | 11/2002 | Daighighian | |
| 2003/0187349 | A1 * | 10/2003 | Kaneko | A61B 6/4014 |
| | | | | 600/425 |
| 2003/0236564 | A1 | 12/2003 | Majercak | |
| 2005/0137520 | A1 | 6/2005 | Rule | |
| 2007/0058778 | A1 | 3/2007 | Coleman | |
| 2010/0198061 | A9 | 8/2010 | Daighighian | |
| 2014/0236145 | A1 * | 8/2014 | Robertson | A61B 6/425 |
| | | | | 606/41 |
| 2017/0000977 | A1 | 1/2017 | Storbeck | |
| 2018/0146936 | A1 * | 5/2018 | Knowland | G01T 1/1617 |
| 2018/0303445 | A1 * | 10/2018 | Subramanian | A61B 6/563 |

OTHER PUBLICATIONS

Atac, et al., Single Fiber Beta Detector for Stereotactic Biopsy and Intraoperative Lumpectomy of Breast Cancer, Fermi National Accelerator Laboratory, presented at the iEEE Nuclear Science Symposium Medical Imaging, Anaheim, California, Nov. 3-9, 1996.

Pain, et al., Arterial input function measurement without blood sampling using a 13-microprobe in rats, Journal of Nuclear Medicine, Oct. 2004, 45:1577-1582.

Senda, et al., Measurement of arterial time-activity curve by monitoring continuously drawn arterial blood with an external detector: Errors and corrections, Annals of Nuclear Medicine, vol. 2, No. 1, 7-12, 1988.

Zimmer, et al., SIC, and Intracerebral !3+-Range-Sensitive Probe for Radiopharmacology Investigations in Small Laboratory Animals: Binding Studies with 11 C-Raclopride, The Journal of Nuclear Medicine, vol. 43, No. 2, Feb. 2002.

Macdonald, et al., Investigation of the Physical Apdects of Beta Imaging Probes Using Scintillating Fiberts and Visible Light Photon Counters, Jun. 1, 2010, UTC from IEEE Xplore.

Janecek, et al., Intravascular Probe for Detection of Vulnerable Plaque, Molecular Imaging and Biology, vol. 6, No. 3, 131-138, 2004.

Pain, et al., SIC an Intracerebral Radiosensitive Probe for In Vivo Neuropharmacology Investigations in Small Laboratory Animals: Prototype Design, Characterization and In Vivo Evaluation, IEEE Transactions on Nuclear Science, vol. 49, Issue: 3, Jun. 2002.

Pain, et al., SIC, an Intracerebral Radiosensitive Probe for In Vivo Neuropharmacology Investigations in Small Laboratory Animals: Theoretical Considerations and Physical Characteristics, IEEE Transactions on Nuclear Science, vol. 47, No. 1, Feb. 2000.

Laymon, et al., Evaluation of a commercial radiochromatography module as an arterial blood activity monitor, Physics in Medicine and Biology, 53 (2008) 339-351.

Balasse, et al., PIXSIC: A Wireless Intracerebral Radiosensitive Probe in Freely Moving Rats, Molecular Imaging, Sep. 2015.

Maramraju, et al., A LSO Beta Microprobe for Measuring Input Functions for Quantitative Small Animal PET, IEEE Nuclear Science Symposium Dec. 2006.

Woody, et al., A Study of Scintillation Beta Microprobes, IEEE Transactions on Nuclear Science 49(5):2208-2212.

Lee, et al., A positron-probe system for arterial input function quantification for positron emission tomography in humans, Review of Scientific Instruments 79, 064301 (2008).

Hosokawa, et al., A Catheter-Based Intravascular Radiation Detector of Vulnerable Plaques, The Journal of Nuclear Medicine, vol. 47, No. 5, 2006.

* cited by examiner

PRIOR ART

PRIOR ART

PRIOR ART
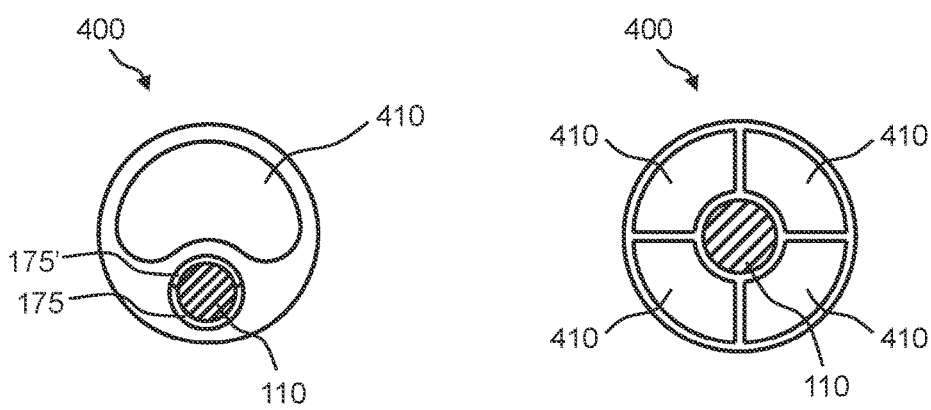
FIG. 5A                    FIG. 5B
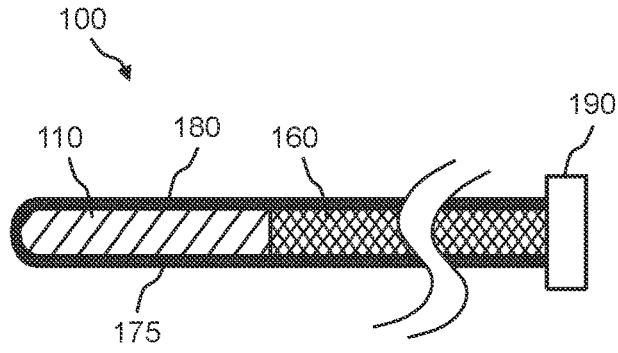
FIG. 6

PRIOR ART

PRIOR ART

100

110        910        160

1000

110              160

PRIOR ART

PRIOR ART

PRIOR ART

PRIOR ART

PRIOR ART

PRIOR ART

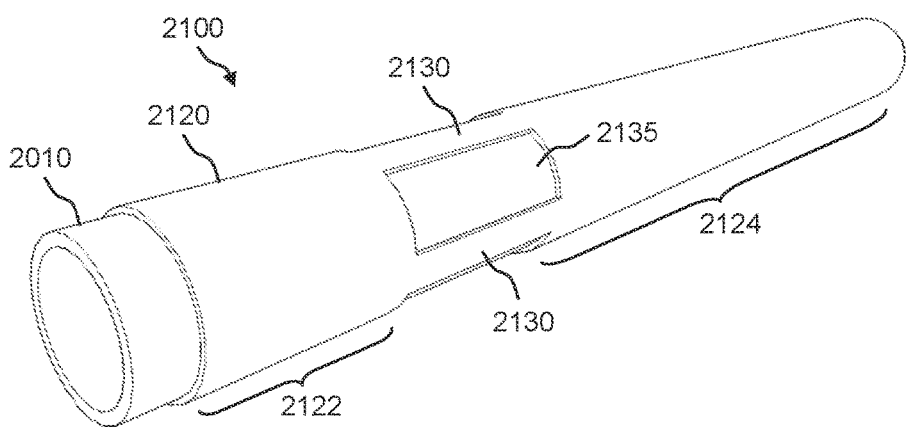
*FIG. 21A*
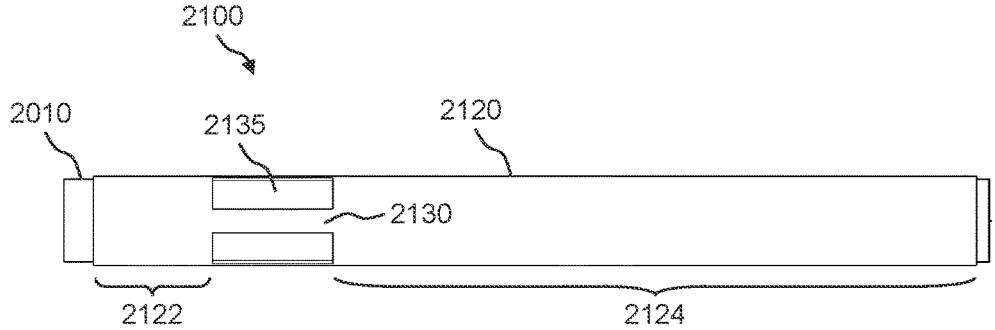
*FIG. 21B*

PRIOR ART

IN VIVO MEASUREMENT SYSTEM AND METHOD FOR THE LOCALIZED MEASUREMENT OF RADIOTRACER CONCENTRATION IN THE BODY

RELATED APPLICATION

The present application claims priority to U.S. Non-Provisional patent application Ser. No. 17/326,445 filed May 21, 2021, the disclosure of which is incorporated herein by reference in its entirety.

TECHNICAL FIELD

The present disclosure relates generally to a device and/or system for the localized measurement of radiotracers in fluids or tissue. More specifically, the present disclosure relates to (1) various embodiments of devices and systems configured for, among other things, the in-vivo measurement of radioactive material (RAM) in the tubing used to administer radiopharmaceuticals for diagnosis or radiotherapy; RAM in blood within various types of blood vessels; the in-vivo measurement of RAM in various tissues accessed through angiography, such as the liver, heart and brain; and the ex-vivo measurement of RAM in other biological compartments; and (2) analogous measurements of RAM in non-biological fluids flowing through fabricated industrial conduits. The present disclosure further provides systems, devices, and methods of measuring RAM concentration within fluids of interest, for example, blood or industrial fluids. In some embodiments, RAM concentration may be determined by taking RAM measurements from a known volume of fluid over a desired period of time.

BACKGROUND

The present disclosure offers certain improvements in a variety of different contexts. For example, many physiological studies, including those in which the outcome measure is analogous to a rate of metabolism of a biological substance, or the concentration of a target protein on cell surfaces, or the activity of enzymes in tissues, and the like, use compartmental modeling to solve the rate equations which requires measuring the change in the concentration of a radiotracer available in the blood supply over time. To obtain this "arterial input function" (AIF), multiple samples of the fluid of interest, such as, for example, blood, must be aspirated from the conduit, for example a blood vessel (including arteries), and analyzed in vitro. Repeatedly drawing blood from a cannulated artery is currently accepted as the most rigorous way to characterize the AIF in medical research. While many investigators have shown that it is feasible to perform serial arterial punctures within some subjects, tolerance for such research procedures can vary in populations that have various types of complicating medical issues, and can lead to a diminished patient experience generally.

Furthermore, repeated punctures may slow subject accrual or contribute to subject dropout rates in longitudinal studies. Risks may also increase in aging populations who require medications for co-morbid conditions that have an effect on the blood clotting cascade. Even when the procedure goes relatively well from the perspective of the patient, many sources of variance enter the system and adversely affect the precision of measurement. Confounds may include challenges in aspirating standard amounts of blood that have not been diluted with the saline solutions that keep catheters from clotting shut, estimating the mean time of aspiration for a process that takes time to complete, problems synchronizing clocks between the various measurement devices, and many others.

In other contexts, angiography and the selective intra-arterial administration of RAM for the treatment of cancer is a growing field. Evidence continues to mount that loco-regional radiotherapy reduces morbidity and prolongs survival in patients with a variety of cancers. At this time, delivery of the RAM from the injection vial to the intended site must be inferred. While it is possible to measure decreases in radioactivity in the injection vial with an external measuring device based on, for example, gas ionization chamber technology, and it is possible to administer radiopaque contrast to follow the flow of fluids through the catheters and selected arteries, it is not possible to measure RAM in the selected arterial system, including RAM concentration, in real time while the procedure is in progress. Additionally, reliance on radiopaque contrast material to detect backflow to tissues that should not be treated increases the risks of radiation-induced injuries to bystander tissues.

Accordingly, there remains a need to overcome the challenges associated with measuring the levels or concentrations of radiotracer available in a vessel or other area in the body over a certain period of time.

SUMMARY

The present disclosure relates generally to a device for the localized measurement of radiotracers in a blood vessel of interest. In some embodiments, the device may include a cannula sized and configured for insertion into the blood vessel of interest.

The cannula may include a measurement chamber portion that may be of a known volume having a first diameter. The cannula may also include a plunger receiving portion having a second diameter larger than the first diameter of the measurement chamber portion. The cannula may also include an opening located, for example, at a distal end of the cannula.

In some embodiments, the device may also include a plunger that may be disposed in the cannula. The plunger may, in some embodiments, include a plunger end portion having a diameter that corresponds to the first diameter of the measurement chamber. The plunger end portion may also be translatable from a first position substantially within the plunger receiving portion to a second position substantially withing the measurement chamber portion.

The device may, in some embodiments, also include a radiation detector. The radiation detector may be positioned proximate the measurement chamber for detecting radiation emitted from blood within the measurement chamber. The radiation detector may also be positioned in any other desirable location.

In some embodiments, the plunger disposed in the cannula may include a plunger end portion having a diameter that corresponds to the first diameter of the measurement chamber. In some embodiments, the plunger end portion may be operatively translatable from a first position in the plunger receiving portion to a second position in the measurement chamber portion. In some embodiments, the second diameter may be such that material is free to flow through the cannula when the plunger is disposed in the first position.

In some embodiments, the radiation detector may include scintillation material that emits light when impacted with particles emitted from a radioactive material. At least a portion of that light may, in some embodiments, be received by an optical connector. In some embodiments, the light may propagate along the fiber optic material to the optical connector. The optical detector may be enabled to convert received light into an electrical signal for processing.

In some embodiments, the cannula may include needle material, and that material may be operatively removable from the cannula after the cannula is positioned within a blood vessel of interest.

In some embodiments, the plunger may be sized and configured to remove residual radioactive material from the measurement chamber upon translating the plunger from the first position to the second position. The plunger may also be utilized to draw blood into the measurement chamber.

The plunger may further be utilized to act as a seal proximate the end of the measurement chamber opposite the opening such that the plunger receiving portion is fluidly separated from the measurement chamber.

In some embodiments, the device may further include a particle absorption material. The particle absorption material may be arranged so as to substantially surround the measurement chamber and the radiation detector for shielding the radiation detector from radiation emitted from sources outside the measurement chamber.

In some embodiments, the particle absorption material may extend fully about the circumference of the measurement chamber. In some embodiments, the particle absorption material may be a metal foil, among other suitable materials as described more fully herein.

BRIEF DESCRIPTION OF THE DRAWINGS

Figure 1:
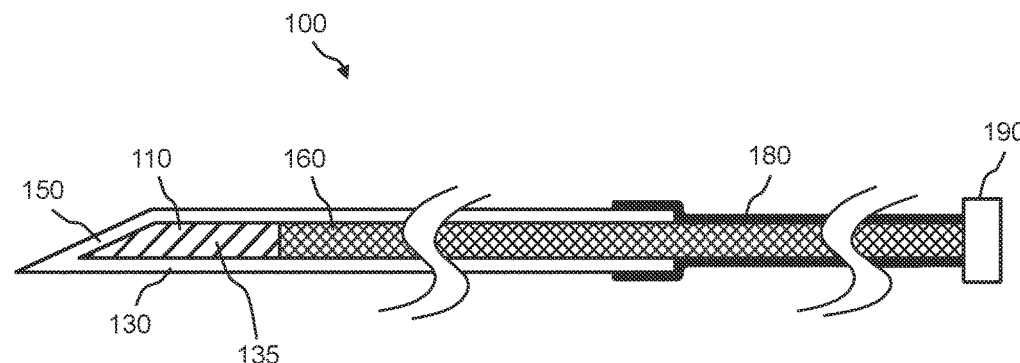

Having thus described the presently disclosed subject matter in general terms, reference will now be made to the accompanying Drawings, which are not necessarily drawn to scale, and wherein:

FIG. 1 illustrates a side view cross section of an exemplary closed end scintillator needle according to one aspect of the present disclosure.

Figure 2:
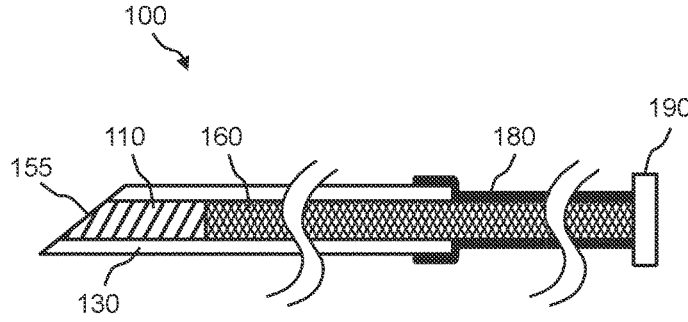

FIG. 2 illustrates a side view cross section of an exemplary open end scintillator needle according to another aspect of the present disclosure.

Figure 3:
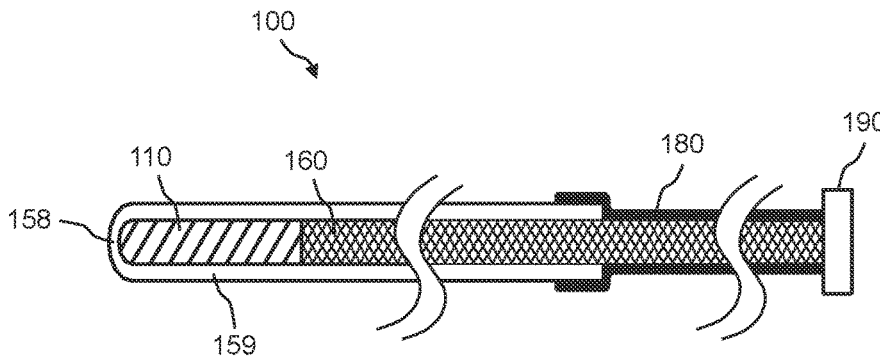

FIG. 3 illustrates a side view cross section of an exemplary blunt end scintillator probe according to another aspect of the present disclosure.

Figure 4:
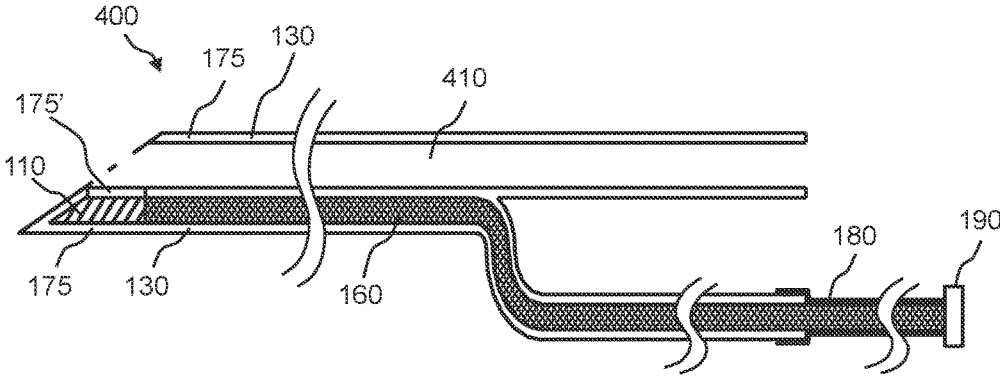

FIG. 4 illustrates a side view cross section of an exemplary scintillator cannula according to another aspect of the present disclosure.

FIG. 5A illustrates a cross sectional view along a longitudinal axis of an exemplary scintillator cannula as shown, for example, in FIG. 4, according to another aspect of the present disclosure.

FIG. 5B illustrates a cross sectional view along a longitudinal axis of an alternative exemplary scintillator cannula similar to the cannula shown in FIG. 4, but having more than one delivery lumen, according to another aspect of the present disclosure.

FIG. 6 illustrates a side view cross section of yet another blunt end scintillator probe according to other aspects of the present disclosure.

Figure 7:
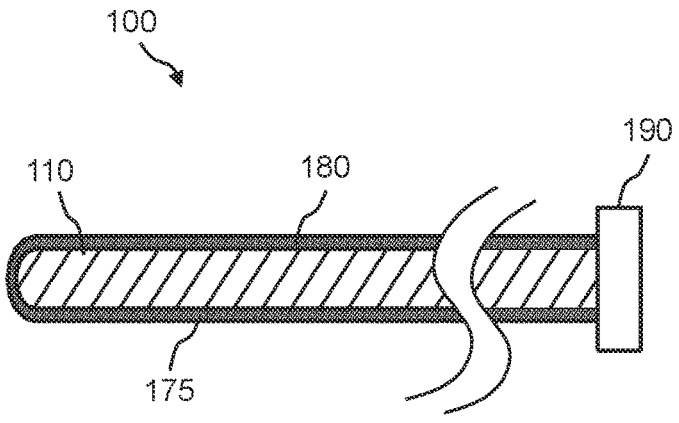

FIG. 7 illustrates a side view cross section of yet another blunt end scintillator probe according to other aspects of the present disclosure.

Figure 8:
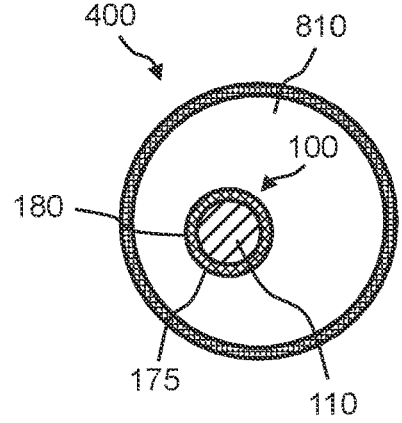

FIG. 8 illustrates cross sectional view along a longitudinal axis of an alternative exemplary embodiment of the present disclosure, wherein the probe taught for example in FIG. 7 is deployed inside, for example, a catheter.

Figure 9:
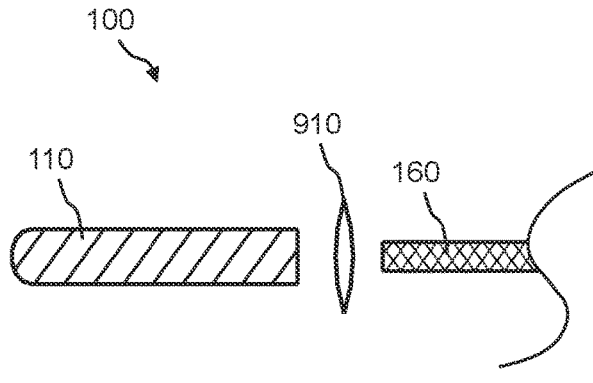

FIG. 9 illustrates a side view cross section of an exemplary embodiment of the present disclosure employing a lens for, among other things, focusing scintillation light.

Figure 10:
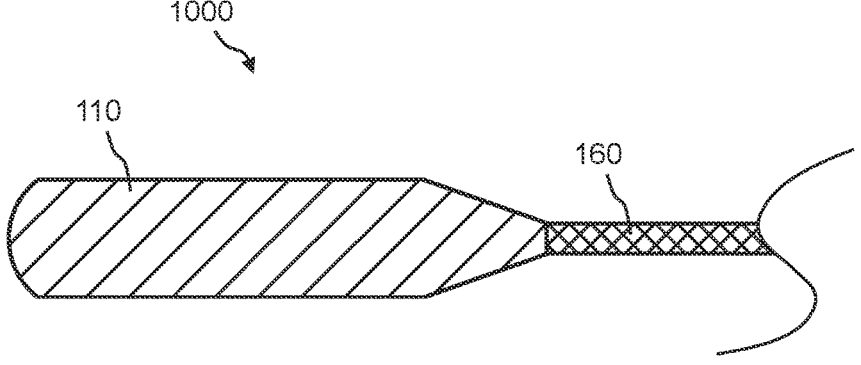

FIG. 10 illustrates a side view cross section of yet another embodiment of the present disclosure wherein the scintillation material may be shaped for purposes of, for example, focusing scintillation light.

Figure 11:
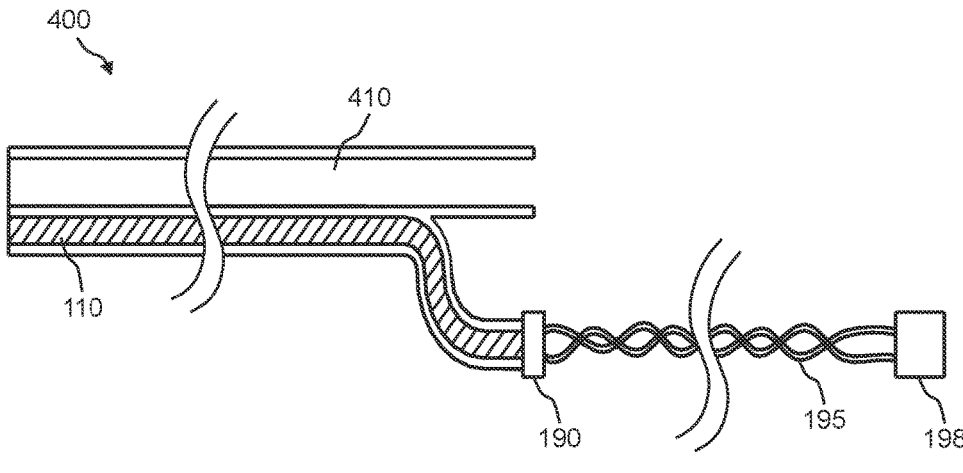

FIG. 11 illustrates a side view cross section of an alternative embodiment of the present disclosure that includes an optical detector coupled to the scintillation material, along with associated electric cabling that may be utilized to transmit an electric signal from the optical detector for processing.

Figure 12:
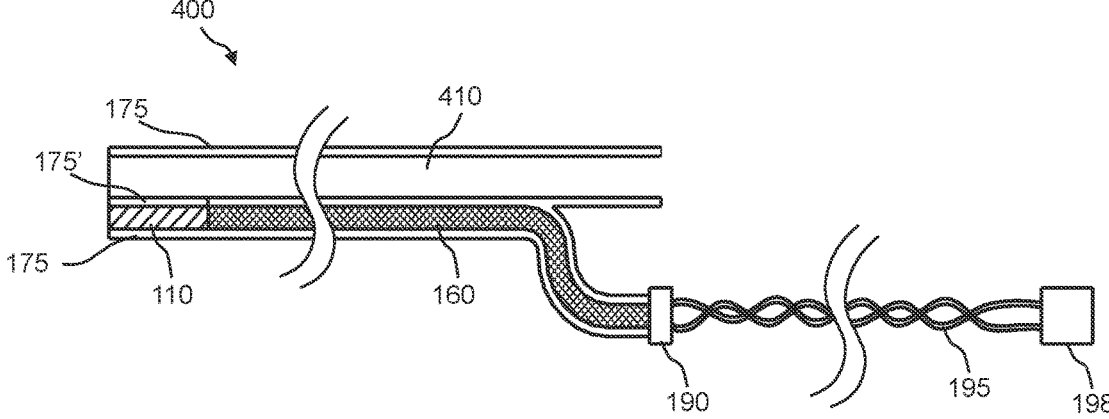

FIG. 12 illustrates a variation of the embodiment shown in FIG. 11 that includes a relatively small portion of fiber optic material between the scintillation material and the optical detector.

Figures 13, 14:
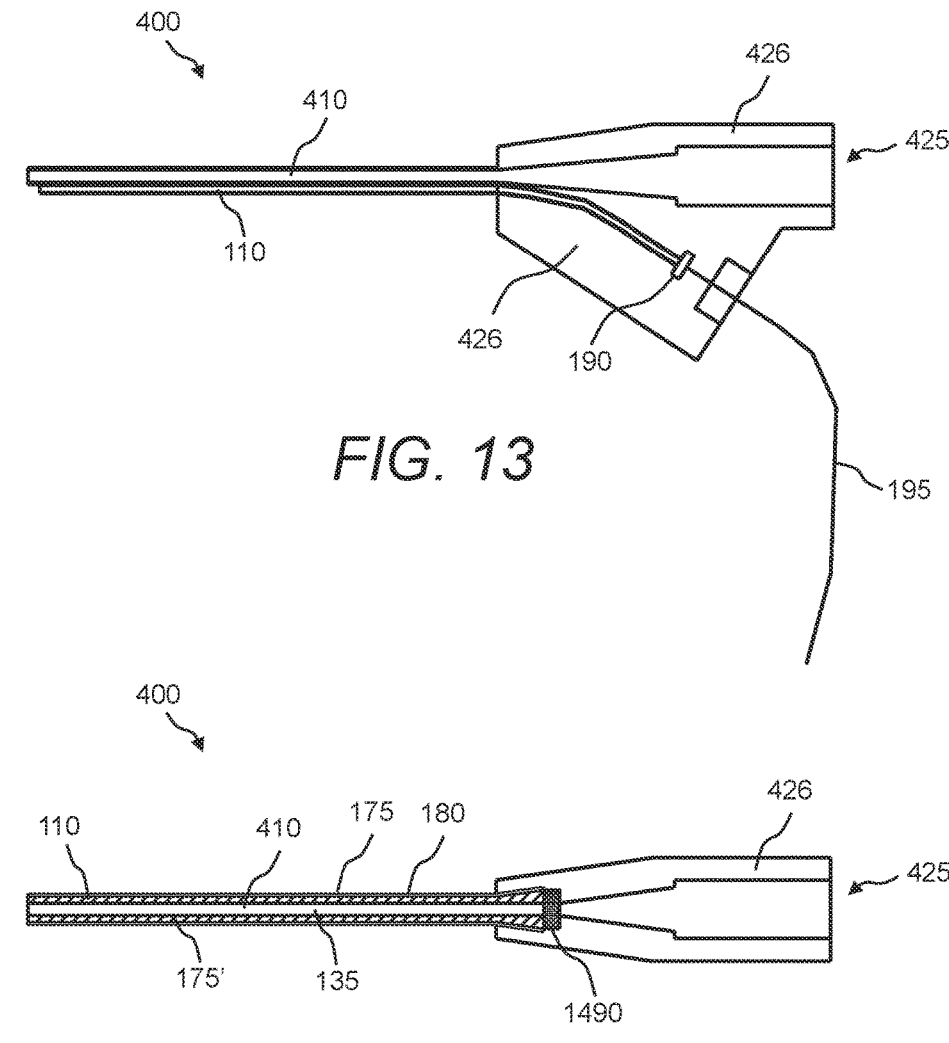

FIG. 13 illustrates a side view cross section of yet another embodiment of the present disclosure that includes scintillation material adjacent a length of a delivery lumen and terminating within material surrounding a delivery hub.

FIG. 14 illustrates a side view cross section of another embodiment similar to that illustrated in FIG. 13, but wherein the delivery lumen itself includes or is constructed from scintillation material.

Figure 15A:
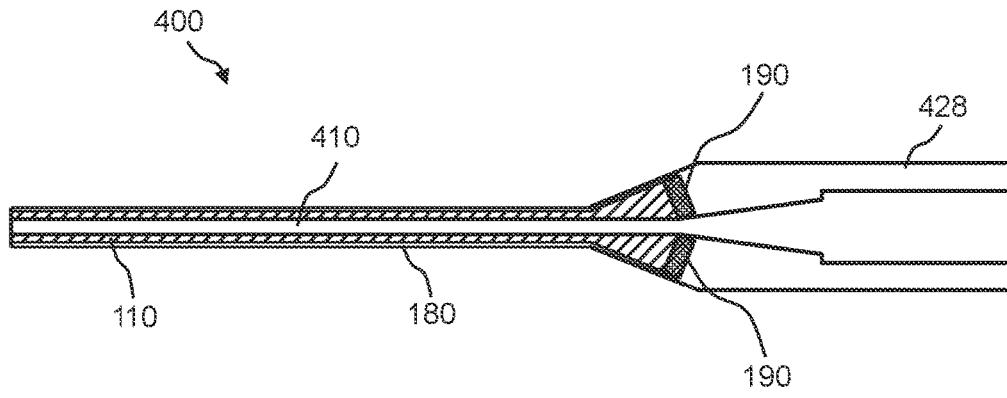

FIG. 15A illustrates a side view cross section of another embodiment similar to that illustrated in FIG. 13, but wherein one or more light detectors are mounted at a longitudinal end of the scintillation material/delivery lumen.

Figure 15B:
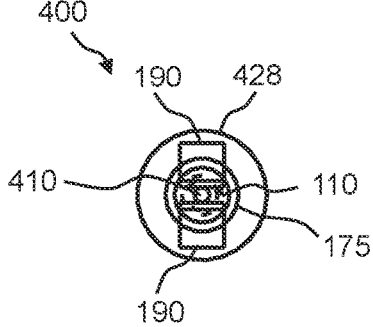

FIG. 15B illustrates a longitudinal side view cross section of the device illustrated in FIG. 15A.

Figure 16:
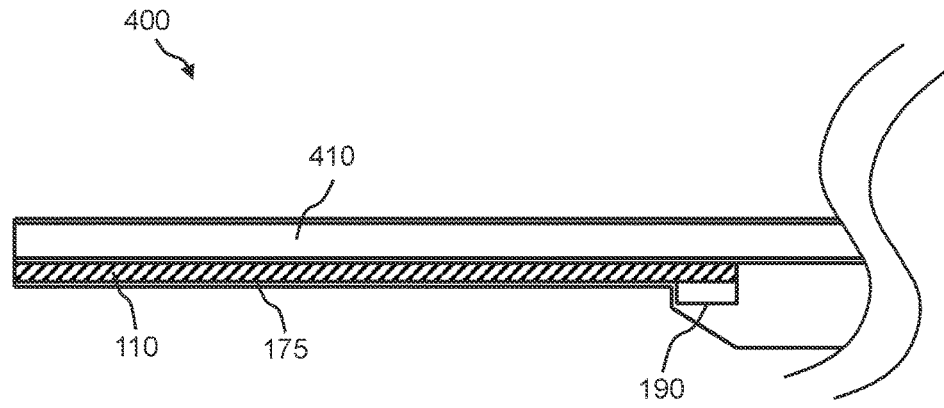

FIG. 16 illustrates a side view cross section of another embodiment of the present disclosure wherein one or more light detectors are positioned radially on the scintillation material.

Figure 17:
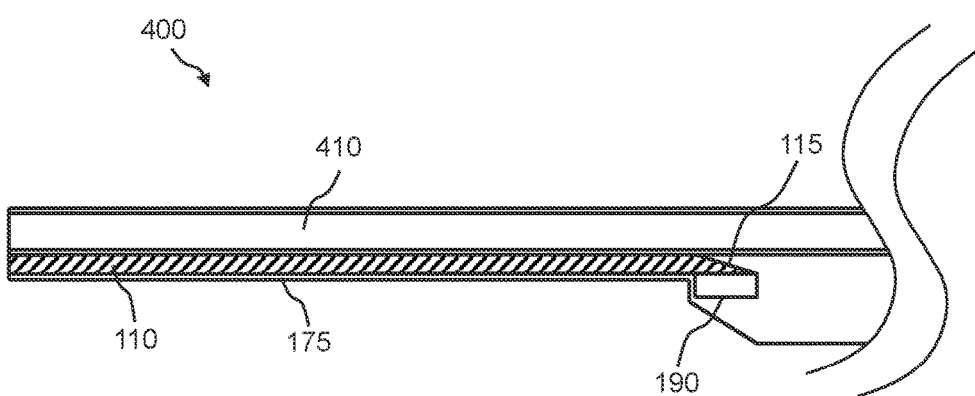

FIG. 17 illustrates a variation of device illustrated in FIG. 16 wherein the scintillation material may include a redirecting surface to redirect light traveling along the longitudinal axis of the scintillation material to a more radial direction.

Figure 18:
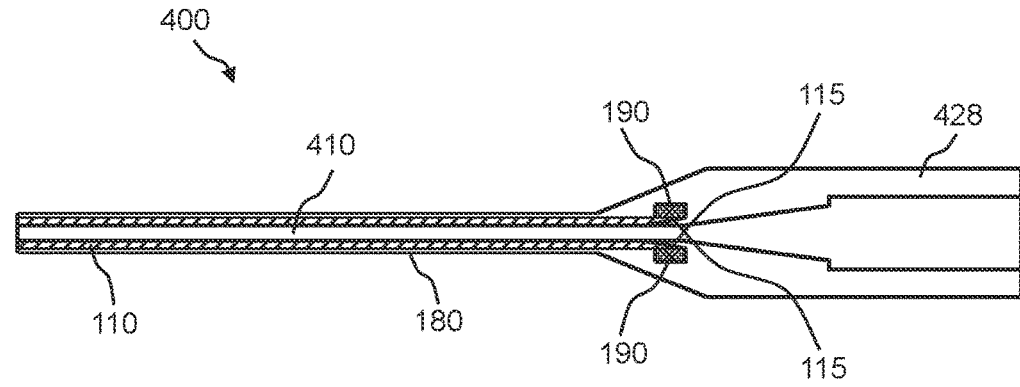

FIG. 18 illustrates a side view cross section of another embodiment of the present disclosure wherein four light detectors are positioned radially around a circular scintillation material to capture incident light.

Figure 19:
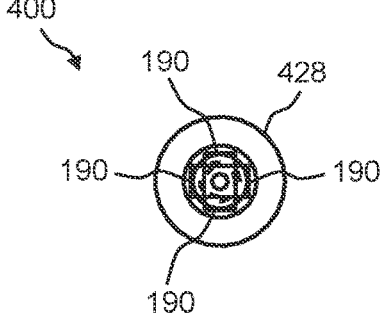

FIG. 19 illustrates a longitudinal cross section of the embodiment shown in FIG. 18.

Figure 20A:
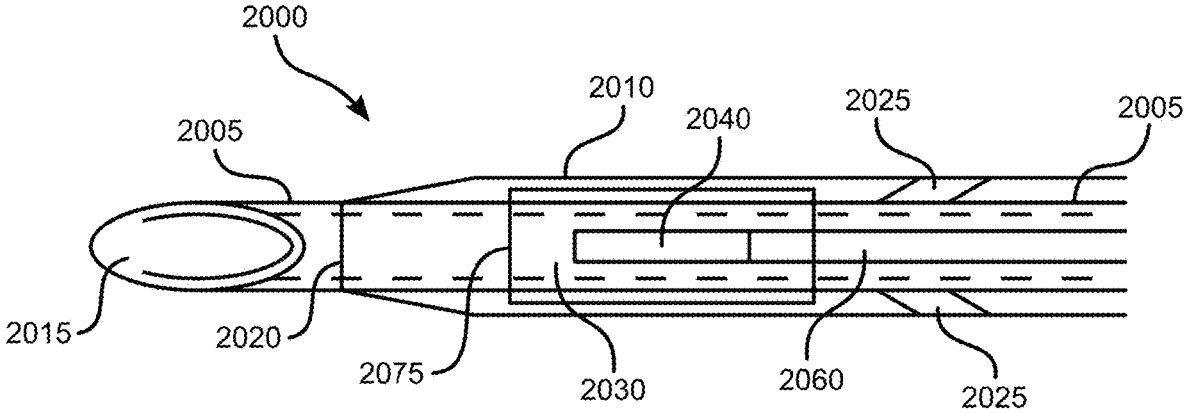
Figure 20B:
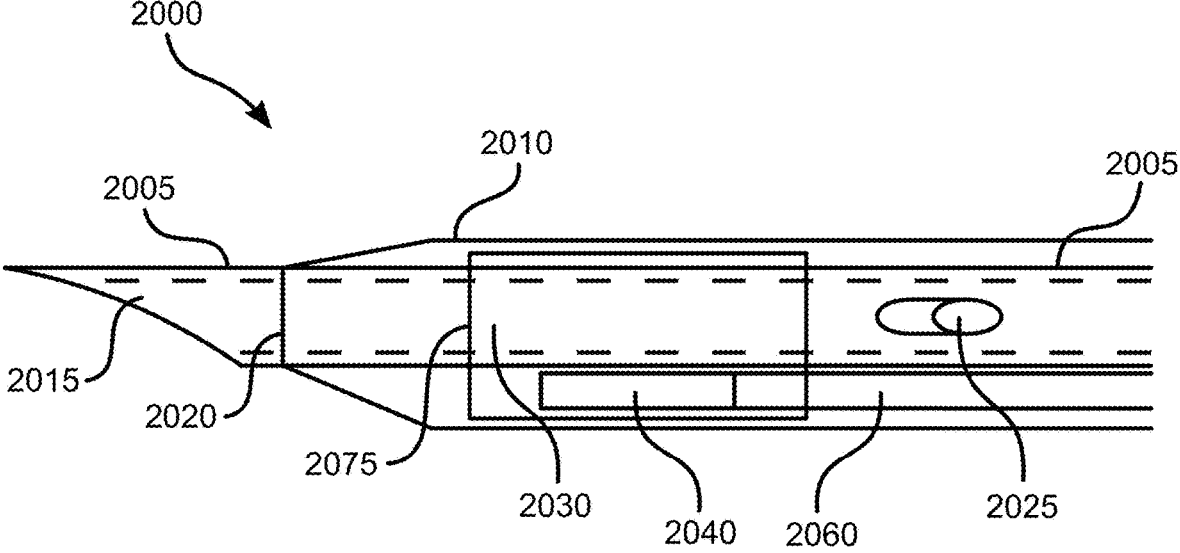

FIGS. 20A and 20B illustrate various views of an exemplary device including a measurement chamber according to certain aspects of the present disclosure.

FIG. 21A and FIG. 21B illustrate side and perspective views, respectively, of an exemplary vessel blocking mechanism and mechanism for substantially centering the presently disclosed devices in a blood vessel of interest, in a first retracted position, according to one embodiment.

Figure 22A:
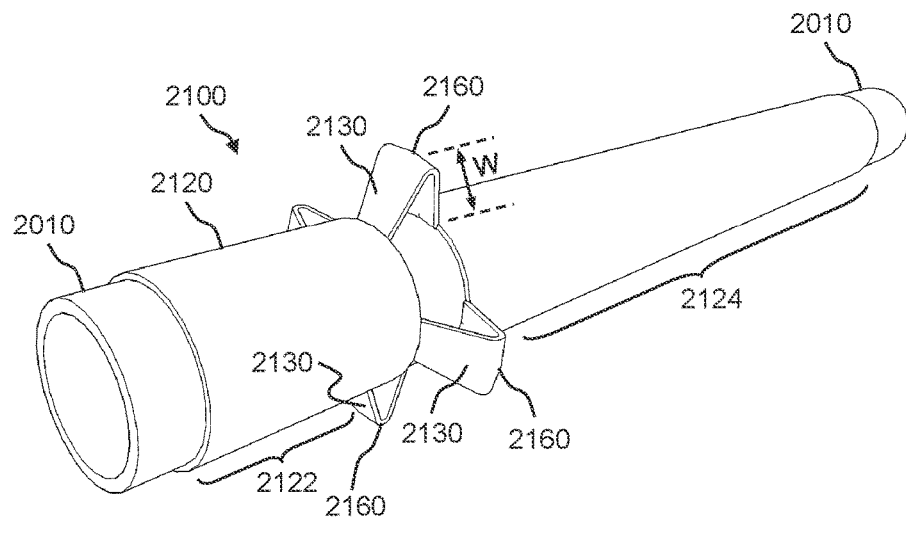
Figure 22B:
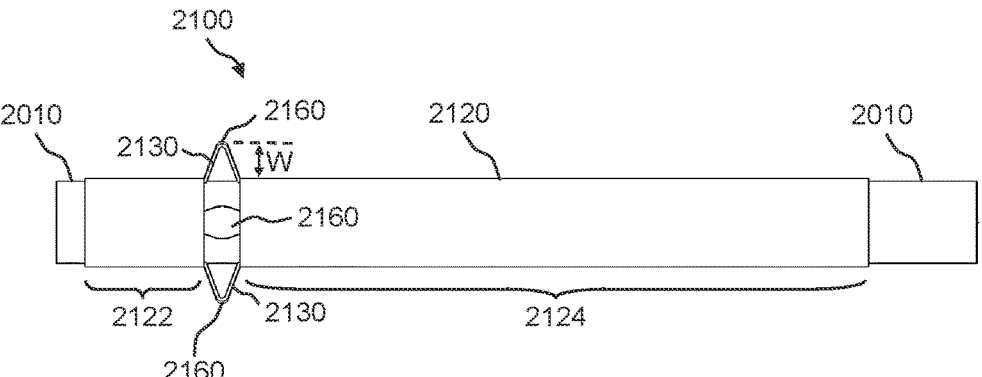

FIG. 22A and FIG. 22B illustrate side and perspective views, respectively of the mechanism in FIG. 21A and FIG. 21B, but in a second extended position.

Figure 23:
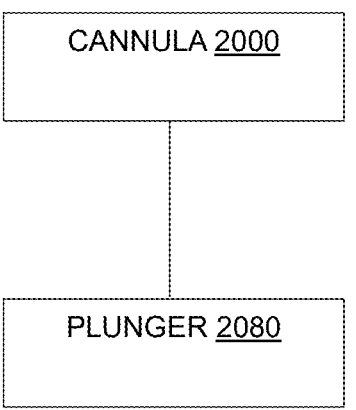

FIG. 23 illustrates a schematic diagram of a cannula associated with a plunger.

DETAILED DESCRIPTION

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In some embodiments, known radiation detectors such as scintillation materials, including for example, organic, inorganic, and/or plastic scintillation materials, may be configured to be inserted into a fluid carrying vessel (e.g., a blood vessel) for use in measuring levels of RAM in the fluid carried within the vessel. Such scintillation materials are known to interact with certain RAM and generate light in response. Such light can then be detected using various detectors and used to determine the presence of, and if applicable the level of, RAM in the fluid. Such scintillation materials may also be used to measure the presence of, and if applicable the level of, RAM in tissues in the body, or other materials.

Plastic-based scintillation fibers are commercially available in the art. Such plastic-based scintillation fibers typically consist of scintillation material incorporated into a plastic resin which is then extruded into thin fibers. Commonly available sizes include diameters from 0.25 mm to 5 mm. Of course, any suitable scintillation material may be employed depending on the application. Suitable scintillation materials, and systems and methods for externally detecting, measuring, and analyzing signals to determine the levels of RAM present in an area of interest are known by those having skill in the art, such as, for example, the systems and methods taught in U.S. Pat. No. 9,002,438 and/or U.S. patent application Ser. No. 14/678,550, both of which are incorporated herein by reference in their entirety.

Referring now to FIG. 1, an exemplary embodiment of a scintillator probe 100 according to some embodiments of the present disclosure is presented. The exemplary scintillator probe 100 presented in FIG. 1 may include scintillation material 110 within a needle 130 formed from any suitable needle material. In some embodiments, the scintillation material 110 may be positioned within a hollow core 135 of the needle 130. In some embodiments, the needle 130 may have a closed end 150, such that scintillation material 110 may be substantially enclosed within needle 130. The hollow core 135 of the needle 130 may further include fiber optic material 160 capable of propagating or transmitting light emitting from the scintillation material 110 to an optical connector 190. Various embodiments of the present disclosure could use the optical connector 190 to couple the scintillator probe 100 to a separate optical sensor (not pictured) for measurement of the light signal. Any known or later discovered fiber optic material 160 may be utilized based on the application for the device. In some embodiments, light shielding material 180 may be utilized to, among other things, prevent unwanted external light from being transmitted to the scintillation material 110, fiber optic material 160, and/or the optical connector 190. Any appropriate light shielding material 180 may be utilized as needed to prevent, for example, contamination from unwanted light.

It will be understood that the fiber optic material 160 may be used to propagate or transmit the light signal generated in the scintillation material 110 to optical connector 190 that may be located substantially near or substantially far away from the scintillation material 110 (e.g., outside of the body).

For example, various embodiments of the present disclosure could make use of opaque light shielding materials 180 that are known in the art including, among others, metals, plastics, coatings, sealants, etc. Additionally, a light-proof coating on the outer surface of a scintillation material (e.g., scintillation material 110) or fiber optic transmission material (e.g., fiber optic material 160) can act as a reflector to maintain light within the material(s).

Various embodiments of the present disclosure could make use of fiber optic light transmission materials (e.g., fiber optic material 160) that are known in the art including, for example, glass, plastic, silicone, etc. Various fiber optic materials are commercially available from several suppliers and such materials may be optimized for various wavelengths of light, bend radii, cladding, etc. The optical light transmission materials can also include a bundle of several optical transmission fibers to increase the effective diameter of transmission fiber while maintaining flexibility, strength, and other features, as desired.

Various embodiments of the present disclosure could also include integrated features for automatically centering or positioning the presently disclosed device within the fluid-carrying vessel as needed. Such features can include fins, prongs, protrusions, whiskers, etc. Additionally, holes placed near the tip of the catheter delivery lumen could act during injection as stabilization jets to center the catheter assembly. Various exemplary embodiments of such features are discussed further hereinbelow.

Referring now to FIG. 2, an alternative embodiment of the scintillator probe 100 depicted in FIG. 1 is presented wherein the needle 130 has an open end 155 rather than a closed end (e.g., closed end 150 in FIG. 1). The scintillator probe 100 of FIG. 2 may further include scintillation material 110, needle material 130, fiber optic material 160, light shielding material 180, and/or optical connector 190.

Referring now to FIG. 3, another alternative embodiment of the scintillator probe 100 is presented wherein the scintillator probe includes a blunt end 158. The probe 100 having blunt end 158 may include any suitable probe material 159, including needle material (e.g., needle material 130), plastics, metals, biocompatible variations of plastics or metals, acrylics, and/or any other suitable material known in the art. Probe 100 may also include scintillation material 110 and/or fiber optic material 160. Like the embodiments depicted in FIG. 1 and FIG. 2, the scintillator probe 100 depicted in FIG. 3 can also include light shield material 180 and one or more optical connectors 190.

Referring now to FIG. 4 an exemplary scintillator cannula 400 with integrated scintillation material 110 is presented. The scintillator cannula 400 may include a delivery lumen 410 for transmitting material into a vessel being measured (not pictured). Adjacent to or otherwise integrated with the delivery lumen 410 may also be, for example, a needle 130 within which scintillation material 110, fiber optic material 160, light shield material 180, and/or optical connector 190 may also be included.

In some embodiments of the present disclosure, it may be advantageous to limit the effective sensing range of the various scintillator probes taught herein. For example, it is often advantageous to determine the concentration of RAM in a given patient's blood stream (or other area of the body) without having to calibrate the device to the specific vessel size or area of interest in each patient. (i.e., it may be advantageous to use scintillator probes having the same specifications on a multitude of patients having, for example, blood vessels of varying sizes to take the same measurement-concentration of RAM). A difficulty, however, lies in at least the fact that a patient having a larger blood vessel will have more RAM flowing by the sensor at a given period of time relative to a patient with a smaller blood vessel, simply by virtue of the fact that there may be more RAM within the sensing range of the scintillation sensor on one patient relative to another. If, however, the effective sensing range could be limited to a volume falling at or within the vessel volume available in a patient having the smallest blood vessel (i.e. RAM in portions of a larger vessel in a larger patient that is outside the area that the smallest vessel would occupy is not included), then a normalized sensing volume could be utilized across the spectrum of patients, and a more accurate and comparable concentration measurement could be made.

For example, in embodiments where it may be advantageous to measure the concentration of RAM in a blood vessel, it may be desirable to use a probe 100 or cannula 400 designed to have an effective measuring volume approximately equal to the diameter of the smallest blood vessel in which the measurement may be taken (e.g., approx. 5 mm, though other diameters could be used). Accordingly, it may be possible to measure the same volume of space containing RAM (e.g., blood flowing in a blood vessel) in a patient having a smaller blood vessel diameter (e.g., approximately 5 mm) and a patient having a larger blood vessel (e.g., approximately 10 mm). By eliminating, for example, the volume of blood in the larger vessel that lies outside of the exemplary 5 mm effective measurement volume, a more standardized concentration measurement may be taken across a sampling of differently sized patients. Note that other effective volumes may be utilized, including for example vessels approximately 1 mm in diameter to larger vessels that are as much as 20 mm or more in diameter.

Advantageously for purposes of the present disclosure, and as known by those having skill in the art, the distance from which a particle can be detected by scintillation material (e.g., scintillation material 110) is related to: (1) the energy or velocity of the particle when it is expelled from the RAM (for which, the maximum is known in the art for a given RAM); and (2) the rate at which such a particle gives up kinetic energy and decreases in velocity through collisions with other materials in the region (which is also known for a given RAM). Such collision materials may include, for example, water molecules, other materials in the blood travelling through the vessel, and importantly, any other particle absorption materials between the scintillator material 110 and the exterior of the scintillator probe (e.g., light shielding 180 (which may, in some embodiments, extend beyond the areas pictured in the Figures) or other particle absorption materials (discussed further hereinbelow)). Thus, a measurement of the kinetic energy of the particle when interacting with the scintillation material 110 may describe the distance it has traveled since first expelled from RAM. Examples of different types of RAM (i.e., isotopes) that may be used in the body, and their associated energy and known range in water, may include, but are not limited to, the following:

| Isotope | Max Energy (MeV) | Max Range in Water (mm) |
|---|---|---|
| Carbon-14 | 0.156 | 0.3 |
| Sulfur-35 | 0.166 | 0.4 |
| Lutetium-177 | 0.49 | 1.6 |
| Iodine-131 | 0.606 | 2 |
| Fluorine-18 | 0.635 | 2.4 |
| Carbon-11 | 0.961 | 3.9 |
| Nitrogen-13 | 1.19 | 5.1 |
| Phosphorus-32 | 1.709 | 7.6 |
| Oxygen-15 | 1.723 | 8 |
| Gallium-68 | 1.899 | 8.9 |
| Yttrium-90 | 2.281 | 11 |
| Rubidium-82 | 3.35 | 17 |

Accordingly, and referring again to FIG. 4, various embodiments of the cannula 400 may also include one or more particle absorption materials 175, wherein the particle absorption material 175 may be configured to have a first energy blocking threshold. Use of such particle absorption materials 175 may advantageously limit the effective volume from which particles emitted by RAM may be detected. Particle absorption material 175 may include, among other things, light shielding material 180, needle material 130, probe material 159, and/or any other material capable of blocking all or a desired portion of particles having energies below the desired threshold. Examples of other suitable particle absorption materials may include, but are not limited to, one or more of aluminum, titanium, nitinol (nickel-titanium), gold, silver, cobalt-chrome, stainless steel, PMMA (poly(methyl methacrylate)), PVC (polyvinyl chloride), polyethylene, PEEK (polyether ether ketone), Polycarbonate, PEI (polyetherimede), polysulfone, polypropylene, polyurethane, and the like.

Additionally, in some embodiments, it may be advantageous to incorporate particle absorption material 175' having a second energy blocking threshold that may be positioned, for example, substantially between the delivery lumen 410 and the scintillation material 110 to, for example, block unwanted particles emitted from residual RAM remaining in delivery lumen 410 following an injection of RAM into the body. Particle absorption material 175' may be the same as particle absorption material 175 (and/or have a second energy blocking threshold substantially equal to the first energy blocking threshold), or particle absorption material 175' may be distinguishable from particle absorption material 175, and have a second energy blocking threshold distinguishable from the first energy blocking threshold of particle absorption material 175.

Referring now to FIG. 5A, an exemplary cross-sectional view of cannula 400 illustrated for example in FIG. 4 is presented wherein the delivery lumen 410 may include a single lumen extending substantially adjacent a section of scintillation material 110. Once again, cannula 400 may include, as desired, one or more layers of particle absorption materials 175 (or 175') to block detection of one or more of residual RAM stuck in delivery lumen 410, and/or reduce the effective measuring volume of the device generally.

Referring now to FIG. 5B, an alternative embodiment of cannula 400 is presented that may include, among other things, more than one separate delivery lumen 410. In some embodiments, the two or more delivery lumens 410 substantially surround scintillation material 110.

Referring now to FIG. 6, FIG. 7, and FIG. 8, various embodiments of the present disclosure are presented wherein a scintillation assembly can be placed through a catheter or existing lumen. In FIG. 6, an example of a scintillation probe 100 comprising scintillation material 110, and/or fiber optic material 160 is presented, wherein all or a portion of the scintillation material 110 may be covered in light shielding material 180. In some embodiments, light shielding material 180 may be, or may also include, particle absorption material 175. In some additional embodiments, the scintillation material 110 in combination with fiber optic material 160 can be of sufficient length to protrude into, for example, a patient's vasculature as well as exit the patient and attach to an external connector 190. FIG. 7 presents another embodiment of probe 100 wherein the scintillation material 110 may extend within the light shielding material 180 (and/or particle absorption material 175) to an optical connector 190 that may be positioned outside a patient's body, thereby obviating the need for any fiber optic material.

Referring now to FIG. 8, a longitudinal cross sectional view of an exemplary cannula 400 having delivery lumen 810 (e.g., a catheter) is presented, wherein probe 100 may be inserted within, or otherwise incorporated into, the lumen 810. Such embodiments could, for example, allow for simultaneous sensing and injecting, among other things. For example, RAM could be injected into the patient via delivery lumen 810, and the level of RAM in a volume to be measured within the patient could be measured using, for example, probe 100 having scintillation material 110 and, if desired, light absorbing material 180 and/or particle absorption material 175.

Various embodiments of probe 100 (or cannula 400) may also make use of one or more lenses such as, for example, lens 910 presented in FIG. 9. Such lenses may, for example, focus light generated within scintillation material (e.g., scintillation material 110) onto fiber optic material (e.g., fiber optic material 160) for transmission to an optical connector or optical sensor (e.g., optical connector 190).

Light may also be focused to the end of a transmission fiber (e.g., fiber optic material 160) by way of, for example, shaping or grinding the scintillation material. Referring now to FIG. 10, exemplary shaped scintillation material 1000 that is shaped in such a manner is presented. Such shaping and/or grinding may be useful, for example, when transitioning between differing diameters of scintillation material 110 and fiber optic material 160, and other scenarios.

In some embodiments, one or more optical detectors for detecting light emitted from scintillation material can be utilized for converting the light signals into electrical signals that may be processed by, for example, a computer or other device, rather than such a device interpreting the optical signal directly. The placement of such optical detectors can vary, and may include for example placement both inside and outside of the vessel containing the fluid to be measured. The electrical signals generated by such optical detectors may also be transmitted using any other appropriate means.

Referring now to FIG. 11, another exemplary embodiment of cannula 400 having delivery lumen 410 is presented wherein an optical detector 190 is in direct contact with scintillator material 110. Such a detector may then convert the optical signal from the scintillator material 110 into an electrical signal that may be transmitted using any appropriate means, including for example, a twisted pair of electrical cabling 195, or other means known in the art (e.g., coaxial cabling, Ethernet, etc.). The electrical cabling 195 may then be coupled to an electrical connector 198 that can then interface as appropriate with a computer or other user interface. Data from detector 190 may also be communicated to a computer other device using any appropriate wireless means, including, for example, Bluetooth, RF, Wi-Fi, etc.

Alternatively, and referring now to FIG. 12, an alternative embodiment of the device illustrated in FIG. 11 is presented, wherein a length of fiber optic material (e.g. fiber optic material 160) may be utilized. In such embodiments, the fiber optic material may be coupled to an optical detector 190 and then transmitted electrically as previously disclosed (e.g., via electrical cabling 195 to electrical connector 198). Cannula 400 of FIG. 12 may also include, as discussed hereinabove, a first layer of particle absorption material 175' having a first energy blocking threshold may be included between the delivery cannula 410 and the scintillation material 110 to, for example, block unwanted particles emitted from RAM remaining in the delivery cannula following injection of RAM into a patient. Further, additional particle absorption materials 175 may be included substantially about the scintillation material 110 and/or the cannula 400 as a whole to block unwanted particles emitted from RAM falling outside of a desired measurement volume (e.g., a volume lying outside of a vessel to be measured).

Referring now to FIG. 13, yet another embodiment of the present disclosure is presented wherein a cannula 400 may be integrated with a delivery hub 425 and an embedded optical sensor 190. Cannula 400 in FIG. 13 may include a length of scintillation fiber 110 that may extend substantially adjacent to the delivery lumen 410. The scintillation fiber 110 may be terminated within material 426 surrounding delivery hub 425 and the light signal generated within the scintillation fiber 110 converted to an electrical or other usable signal at sensor 190 as previously disclosed, and optionally transmitted to a separate user interface, computer or other device (via, for example, wire 195). Such embodiments may have the advantage of providing a single catheter unit that may be used to both administer RAM and/or other materials (via, for example, delivery lumen 410) to the vessel and simultaneously detect RAM (via, for example, scintillation fiber 110) in the vessel. Light shielding material (e.g., light shielding material 180) and/or particle absorption material 175 may also be utilized as appropriate to properly shield the scintillation fiber 110 and/or sensor 190 as appropriate and disclosed hereinabove.

Referring now to FIG. 14, another exemplary embodiment of a cannula 400 is presented wherein the delivery lumen 410 may be itself made in whole or in part of scintillation material (e.g. scintillation material 110). Like cannula 400 illustrated in FIG. 13, the cannula 400 in FIG. 14 may include a single catheter unit wherein the delivery lumen 410 is made, in whole or in part, from scintillation material 110 and forms a hollow core 135 (i.e. delivery lumen 410) that may be used to both administer RAM and/or other materials to the vessel (or extract material from the body) and simultaneously detect RAM in the vessel. In this exemplary embodiment, a ring-shaped light detector 1490 may be employed to better engage with the ring-shaped scintillator material 110 of delivery lumen 410. The ring-shaped light detector 1490 may be disposed within a material 426 surrounding a delivery hub 425. The cannula 400 of FIG. 14 may also include light shielding material 180 and/or particle absorption material 175 (and/or 175') as necessary for preventing light and/or particles from undesirably entering the system or affecting the measurements being taken, as discussed hereinabove.

Referring now to FIG. 15A and FIG. 15B, in some embodiments, two or more light detectors 190 may be disposed, for example, at the axial end of the scintillation material 110 that makes up all or part of delivery lumen 410 such that light generated within the scintillation material 110 travels axially along the scintillation material 110 to the two or more light detectors 190. In various other embodiments, three, four, or any other number of light detectors may be disposed at, for example, the axial end of the scintillation material 110. Light detectors 190 may be disposed equidistant about the longitudinal axis of the delivery lumen 410, or disposed in any other appropriate configuration to receive light generated within the scintillation material. In some embodiments, fiber optic material (e.g., fiber optic material 160) may be included within or otherwise adjacent to the scintillation material 110 in delivery lumen 410 such that light generated within the scintillation material 110 travels axially along the delivery lumen 410 from the scintillation material 130 through the fiber optic material 160 and to the light detectors 190. Light shielding (e.g., light shielding 180) may also be included in cannula 400 as desired and otherwise described herein to prevent exposure of unwanted light to the system and/or light detectors 190. Particle absorption material 175 may also be utilized as discussed hereinabove.

Referring now to FIG. 16, another exemplary embodiment of the presently disclosed cannula 400 is presented wherein scintillation material 110 and light detector 190 may be disposed substantially adjacent a delivery lumen (e.g., delivery lumen 410). In some embodiments, light detector 190 may be disposed radially adjacent to the scintillation material 110 rather than, for example, at the axial end of the scintillation material as shown, for example, in FIG. 15A and FIG. 15B. Particle absorption material 175 may also be utilized as discussed hereinabove. Referring now to FIG. 17, scintillation material 110 may in some embodiments be formed in a manner to create a surface 115 that may be used to, among other things, reflect light traveling substantially along a longitudinal axis of the scintillation material 110 and redirect such light in a substantially radial direction onto one or more light detectors 190. Particle absorption material 175 may also be utilized as discussed hereinabove. FIG. 18 and FIG. 19 include an alternative embodiment of cannula 400 in FIG. 17 that includes a reflective surface(s) 115 and one or more light sensors 190 disposed radially about all or a portion of the scintillation material 110.

In various other embodiments, in may be advantageous to measure RAM contained in a known volume, and thereby determine a concentration of RAM in a fluid and/or area of interest. For example, in some embodiments, a probe or cannula may be configured such that a fluid of interest (e.g., blood) may be drawn into or otherwise flow through a measurement chamber of known volume, and measurements of RAM in the fluid in the chamber at a given time may be taken. By limiting RAM measurements to RAM contained within a fluid within the known volume of the measurement chamber, the RAM concentration (e.g., RAM per unit volume) of the fluid may be determined, providing additional meaningful information to a practitioner or other interested party. In addition, the probe or cannula may also be configured to act as a delivery or extraction device, thereby allowing, for example, the probe or cannula to be inserted into a vessel of interest, RAM to be administered to the fluid system, subsequent measurements of RAM in the fluid taken over a desired period of time from an area (e.g. measurement chamber) of known volume, and if desired, extraction of fluid or other material from the vessel of interest.

A more specific example, according to some embodiments, may include a probe or cannula configured to act as a delivery or extraction device for insertion into a blood vessel of interest. According to some embodiments, the probe or cannula could be used to administer RAM to a patient's blood stream. Then, the same device could be used to take subsequent measurements of RAM in the blood taken over a desired period of time from an area (e.g. measurement chamber) of known volume. If desired, extraction of blood and/or other material from the blood vessel of interest may also be facilitated.

Referring now to FIG. 20A and FIG. 20B, an exemplary cannula 2000 according to some embodiments of the present disclosure is presented. Cannula 2000 may include, in some embodiments, a catheter 2010. Catheter 2010 may be configured for insertion directly into a blood vessel of interest, or in some embodiments may include a needle material 2015 or similar material to facilitate entry into the body and/or a blood vessel of interest. Catheter 2010 may also be delivered to an area of interest through any other practical methods or mechanisms known to those of skill in the art, including insertion through another delivery tube, cannula, etc., whether pre-inserted into the blood vessel of interest or otherwise. In some embodiments, needle material 2015 may be optionally removed from the cannula and/or blood vessel of interest after delivery of the catheter 2010. Cannula 2000 may include one or more plastics, metals, biocompatible variations of plastics or metals, acrylics, and/or any other suitable material known in the art.

In some embodiments, catheter 2010 of cannula 2000 may also include a first opening 2020. In some embodiments, first opening 2020 may be disposed at a distal end of catheter 2010, though other locations for first opening 2020 may be utilized as desired. In certain preferred embodiments, first opening 2020 is a single opening at the distal end of catheter 2010. First opening 2020 may also include two or more openings if desired. In some embodiments, for example, needle material 2015 may extend through the cannula 2000 and out of the first opening 2020, and be optionally retracted into or entirely removed from the cannula 2000 via first opening 2020.

In some embodiments, cannula 2000 may also include a measurement chamber 2030 disposed within cannula 2000. Measurement chamber 2030 may be of any shape or size within cannula 2000. In some preferred embodiments, the volume of measurement chamber 2030 is known, such that the volume of fluid or other material within measurement chamber 2030 may be known. Measurements to be taken from fluids or any other material inside measurement chamber 2030 may include measurements of radiation being emitted from such fluids or materials within the chamber. Accordingly, in some embodiments, a concentration of RAM, for example, may be determined.

To introduce fluid or material (e.g., blood) into the measurement chamber 2030 for measurement, cannula 2000 may enable such fluid to enter via first opening 2020. For example, a negative pressure could be introduced into the cannula using, for example, a plunger 2080 or similar device, to pull fluid into a distal end of the cannula 2000 (e.g., first opening 2020) and into measurement chamber 2030 for measurement. Following measurement or after some other desired period of time, the fluid could be re-inserted into the vessel or extracted out of the vessel and cannula 2000 entirely, as desired.

In certain other embodiments, fluid or material (e.g., blood) may be introduced into measurement chamber 2030 via other mechanisms that may, for example, advantageously allow for more consistent and continuous measurements and/or monitoring. For example, in some embodiments, cannula 2000 may include a second opening 2025. In some embodiments, second opening 2025 may be disposed on an opposite side of measurement chamber 2030 relative to first opening 2020. Accordingly, the fluid or material may be allowed to enter the cannula 2000 via second opening 2025, flow into and through measurement chamber 2030, and then exit cannula 2000 via first opening 2020, thereby facilitating a substantially continuous measurement of the contents of the fluid a desired period of time.

Measurement chamber 2030 may span the entire volume between the openings 2020 & 2025, or may include only a portion of the volume between the openings 2020, 2025. Regardless of how arranged, however, the volume of measurement chamber 2030 may be known, such that the fluid brought into the measurement chamber 2030 has a known volume. Accordingly, because the volume of measurement chamber 2030 may be known, and therefore a volume of the fluid and/or material to be measured within the chamber may be known, a concentration of measured material in the fluid (e.g. concentration of RAM) may be advantageously determined.

In some embodiments, second opening 2025 may be a single opening, while in certain other embodiments, second opening 2025 may include two or more openings. For example, as illustrated in exemplary FIG. 20A and FIG. 20B, second opening 2025 may include four openings disposed substantially equal-radially about cannula 2000, though any number and arrangement of openings may be utilized as desired. Indeed, considerations such as vessel type, fluid viscosity, and other parameters may dictate the number and/or arrangement of second opening 2025 to best facilitate, for example, entry into the measurement chamber 2030 as desired.

Cannula 2000 may also include a sensor or other device for measuring certain contents or properties of the fluid or other material inside the measurement chamber 2030. In some embodiments, cannula 2000 may include a radiation detector 2040 disposed proximate the measurement chamber 2030 such that radiation emitted from fluids or materials within the measurement chamber 2030 may be detected. Radiation detector 2040 may be arranged in any shape or configuration about measurement chamber 2030. For example, radiation detector 2040 may extend about an entire perimeter of the measurement chamber 2030, or as depicted for example in FIG. 20, may extend substantially along one side of measurement chamber 2030.

In some embodiments, radiation detector 2040 may include a scintillation material (e.g., scintillation material 110) as described in detail hereinabove. As discussed, scintillation materials can emit light in response to particles emitted from radioactive materials that impact the scintillation material. The emitted light may be measured directly, or may be transmitted to an optical connector (e.g. optical connector 190) via fiber optic material 2060 (or, for example, fiber optic material 160). Optical connector 190 may be coupled to a light detector or other system for measuring the light emitted as discussed hereinabove.

In some embodiments, it may be advantageous to include mechanisms to minimize or eliminate detection by the radiation detector 2040 of radiation originating from outside of the measurement chamber 2030. In this way, when desired, only radiation emitting from the fluid or material inside the measurement chamber 2030 may be detected, with outside radiation eliminated or at least substantially eliminated, facilitating a substantially accurate measurement of the amount of radioactive material inside the measurement chamber 2030 at any given time.

To eliminate or at least reduce the detection of radiation from outside the measurement chamber 2030, various shielding or "particle absorption materials" may be employed. For example, in some embodiments, cannula 2000 may include particle absorption material 2075, which may be generally similar to particle absorption material 175 discussed hereinabove. As depicted, for example, in FIG. 20, particle absorption material 2075 may be disposed in some embodiments substantially about measurement chamber 2030 such that the measurement chamber 2030 is substantially enclosed. Radiation detector 2040 may also be included within the particle absorption material 2075.

As will be appreciated by those having skill in the art, the arrangement of particle absorption material 2075 depicted in FIG. 20 is but one example, and may take any shape or form as necessary to effectively prevent unwanted radiation from reaching radiation detector 2040. For example, to prevent introduction of radiation along a path passing through the first opening, shielding material may extend downward and/or away from the radiation detector 2040 to preclude particles from certain angles from impacting the detector. In certain other embodiments, radiation from outside of the measurement chamber may be accounted for through algorithms or other means (e.g., eliminating particles below certain energy thresholds). Additionally, in certain other embodiments, if cannula 2000 were to be employed in an area where undesired radiation is known to be located in only one direction relative to cannula 2000, particle absorption material 2075 may only need to be deployed on one side of cannula 2000 to effectively block the undesired radiation. Those having skill in the art will understand how to best shield the measurement chamber and/or radiation detector to best facilitate the measurements desired by the various embodiments of the present disclosure.

In some embodiments, cannula 2000 may also be utilized to facilitate the delivery of RAM to the patient or system. Accordingly, in some embodiments, cannula 2000 may be inserted into a blood vessel of interest, RAM injected into the blood vessel of interest and the circulatory system generally via the cannula 2000, and then measurements of the RAM in the blood over a desired period of time and/or at a particular time may be determined. In some embodiments, cannula may include a delivery sheath 2005. Delivery sheath 2005 may be optionally removeable from cannula 2000 such that after injection of RAM through the delivery sheath 2005, the delivery sheath 2005 may be removed. Benefits of the delivery sheath being removed include, but are not limited to, elimination of any residual RAM from the cannula system that may undesirably affect measurements by the radiation detector 2040, for example. Delivery sheath 2005 may also serve to block or close second opening 2025 until the sheath 2005 is removed, thereby preventing flow of fluids or other materials from the vessel into the measurement chamber 2030 until desired. Delivery sheath 2005 may also reduce or even eliminate the need to "flush" the line with saline or other materials. In some embodiments, delivery sheath 2005 and needle material 2015 may be integrated, and optionally removed/inserted together. In other embodiments, delivery sheath 2005 and needle material may be stand alone components, and/or integrated with other components of cannula 2000 as desired.

In some embodiments, cannula 2000 may require additional components or mechanisms to induce fluid or other material of interest in the vessel to enter the measurement chamber 2030. For example, viscous fluids (like blood, for example) may simply flow around cannula 2000 rather than entering the measurement chamber (for example, through second opening 2025). Accordingly, in some embodiments, it may also be advantageous for cannula 2000 to include a vessel blocking mechanism positioned downstream of the second opening 2025 for at least partially blocking fluid flow through the vessel of interest. In so doing, fluid pressure upstream of the blocking mechanism (e.g., around the second opening 2025) may be higher relative to fluid pressures below the blocking mechanism (e.g., around the first opening 2020), and therefore advantageously induce fluid flow into the second opening 2025, through the measurement chamber 2030, and out of cannula 2000 via the first opening 2020.

In other embodiments, it may also be advantageous to ensure that the probe 100 or cannula 400 or 2000 may be substantially centered within the vessel to ensure that the effective measurement volume is contained within the vessel. In some embodiments, having the probe 100 or cannula 400 or 2000 substantially centered may mean, for example, that the effective measurement volume of the probe 100 or cannula 400 falls within the blood vessel of interest.

Referring now to FIG. 21A and FIG. 21B, an exemplary embodiment of a vessel blocking mechanism 2100 according to one aspect of the present disclosure is presented. The exemplary embodiment presented in FIGS. 21A and 21B may also be used, if desired, to center the system (e.g., cannula 2000) within a vessel of interest. In some embodiments, the vessel blocking system 2100 may be atraumatic and include a catheter 2010 surrounded by a sheath 2120. Sheath 2120 may include, among other things, a first substantially solid portion 2122, a second substantially solid portion 2124, and one or more connecting strips 2130 spaced apart by one or more windows 2135. In some embodiments, sheath 2120 may include four connecting strips 2130, but sheath 2120 may include two, three, five, six, or any other number of strips as desired. In such embodiments, the two or more connecting strips 2130 may each be substantially the same width, or may be of substantially different widths, or any combination thereof as desired. Similarly, windows 2135 may each be substantially the same width, or may be of substantially different widths, or any combination thereof as desired. In various other embodiments, sheath 2120 may also include one solid connecting strip 2130 with no windows 2135, or one connecting strip with one window 2135. In such embodiments, the one connecting strip 2130 may be larger than, smaller than, or the same size as the window 2135.

FIG. 21A and FIG. 21B illustrate the vessel blocking system 2100 in a first "insertion" position according to some embodiments of the present disclosure. In some embodiments, sheath 2120 may be arranged such that when arranged in the first "insertion" position, the second opening 2025 of the cannula 2000 and/or catheter 2010 may be covered by sheath 2120, thereby effectively preventing the flow of any fluid or other material into the measurement chamber 2030. Alternatively, sheath 2120 may include one or more openings (not shown) that correspond to the second opening 2025 of the cannula 2000 such that flow into the measurement chamber 2030 is feasible when in the first "insertion" position shown. Second opening 2025 of cannula 2000 may also align with one or more of the windows 2135 when sheath 2120 is in the first "insertion" position.

Referring now to FIG. 22A and FIG. 22B, a second "activated" position of the vessel blocking system 2100 is presented according to some embodiments of the present disclosure. For example, in some embodiments, the first solid portion 2122 and second solid portion 2124 may be movable relative to each other and/or catheter 2010 (e.g., capable of sliding along catheter 2010). In some embodiments, catheter 2010 is a 22-gauge (0.9 mm) catheter, but the catheter may also range as desired from about 14 gauge to 26 gauge, and/or below 14 gauge and above 26 gauge if desired. The second solid portion 2124 may also be operatively movable along catheter 2010 relative to first solid portion 2122 such that second solid portion 2124 may operatively slide along catheter 2010 towards and relatively adjacent to first solid portion 2122 as depicted in, for example, FIG. 22A and FIG. 22B. In so moving, in some embodiments, connecting strips 2130 may be compressed, causing connecting strips 2130 to bulge outwards as shown, for example, in FIG. 22A and FIG. 22B, thereby forming wings 2160.

Wings 2160 may act as a vessel blocking mechanism, and may also advantageously act to substantially center the system in the vessel. By varying the length of connecting strips 2130, the effective radial width of the wings "W" can be advantageously varied along with the effective diameter of the catheter 2010 and sheath 2120 to accommodate any desired vessel diameter (e.g., ensure that the overall combined width of the wings "W" do not extend beyond a minimum vessel diameter so as to prevent damage to, among other things, the vessel wall(s)). The dimensions may also be controlled to vary the among of blocking of the vessel desired, and therefore impact the amount of relative pressure differential created between the second opening 2025 and first opening 2020, for example. Further, by varying the relative distance between first solid portion 2122 and second solid portion 2124, the length "W" can be varied in real time, as desired.

In some embodiments, sheath 2120 may also include one or more openings (not shown) that substantially align with second opening 2025 of cannula 2000 when sheath 2120 is in the second "activated" position. In some embodiments, the one or more openings that correspond with second opening 2025 may be disposed on second solid portion 2124. In certain other embodiments, second opening 2025 may align with the one or more strips 2030 such that second opening 2025 is "opened" when sheath 2120 is in the second "activated" position. In certain other embodiments, second opening 2025 of cannula 2000 may align with the one or more windows 2135 such that second opening 2025 is not blocked by sheath 2120 in either the first or second position.

In some embodiments, the total diameter of the catheter system 2100 with wings 2160 in the activated (i.e. extended) position is approximately 5 mm, but may be less than 5 mm and as large as 10 mm or more if desired. In some embodiments, the radial width W of wings 2160 may be approximately one-half the length of connecting strips 2130. In other embodiments, the radial width W of wings 2160 may be less than one-half of the length of connecting strips 2130.

In some embodiments, sheath 2120 may be configured such that sheath 2120 defaults to the first "insertion" position as depicted in FIG. 21A and FIG. 21B. In such embodiments, connecting strips 2130 may be of a such rigidity that strips 2130 tend to push first solid portion 2122 and second solid portion 2124 apart from one another. In various other embodiments, sheath 2120 may be configured such that sheath 2120 defaults to the second "activated" position as depicted for example in FIG. 22A and FIG. 22B. In such embodiments, connecting strips 2130 may include metal or other rigid material that default to the activated position but extend substantially flat to the first "insertion" position when second solid portion 2124 is made to slide away from first solid portion 2122. It is also contemplated that in some embodiments, first solid portion 2122 and second solid portion 2124 are not entirely solid, but may include any composition suitable for causing the compression or expansion of connecting strips 2130 described hereinabove. For example, first solid portion 2122 and/or second solid portion 2124 may include strips of material, a lattice structure, or other structurally suitable configuration. Sheath 2120 may be made from any suitable material, including among other things biocompatible metals, plastics, and the like.

In other embodiments, cannula 2000 may generate a pressure differential to induce flow through the measurement chamber 2030 in other ways. For example, cannula 2000 may include mechanisms for generating a lower pressure at the first opening 2020 relative to second opening 2025, for example, by using curved wings or other fluid dynamics principles.

Characteristics of certain fluids may call for additional features not already provided for herein. By way of just one example, for devices to be used in blood vessels, the clotting characteristics of blood may need to be taken into consideration. For example, it may be advantageous to coat all or part of the various probes and cannulas described herein in materials known to have anti-coagulation properties, or use such materials for the probes and cannulas themselves. Anti-coagulation materials are known to those having skill in the art, and include but are not limited to, new liquid infused structured surfaces, and the use of anti-coagulation drug coatings on the portions of the cannula or probe that will be primarily in contact with the blood, among other things.

Other mechanisms for minimizing coagulation of blood can include mechanisms for introducing turbulence to the flow. Turbulence may be induced, for example, by use of non-uniform flow surfaces, or other means for introducing turbulence to the flow to further reduce coagulation.

According to some embodiments, the present disclosure also provides for a method of using scintillation probe disclosed hereinabove. In some embodiments, a scintillation probe as taught herein may be inserted to a patient's blood vessel. In some embodiments, a mechanism (e.g., sheath 2120) may be utilized to substantially center the probe in the vessel and/or to act as a vessel blocking mechanism to create a pressure differential between the second opening 2025 and first opening 2020. The probe or cannula may then measure the presence of, and/or the level of, RAM in the blood contained within the vessel in real time, or in some embodiments, measure RAM in the blood contained within a measurement chamber of the cannula having known volume such that a concentration of RAM in the blood may be determined. Various means for capturing and displaying the presence or levels of RAM in the blood may be utilized, including those taught in U.S. Pat. Nos. 9,002,438 and 9,939,533, and U.S. Patent Pub. Nos. 2021/0015434 and 2015/0276937, each of which are incorporated herein by reference in their entireties.

The present disclosure further contemplates use of various embodiments in industrial settings. For example, variations of the present disclosure could be used to measure RAM in any fluid carried within any fluid carrying vessel. For example, RAM levels could be measured in oil pipelines for use in detecting the presence of leaks or other flow issues. While examples of use in relation to blood vessels is discussed in detail above, the inventors do not intend such disclosure to be limiting and expressly contemplate use of scintillation materials in any type of fluid-carrying vessels for measuring the presence of or level of RAM in a fluid carried therein.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments +50%, in some embodiments ±20%, in some embodiments +10%, in some embodiments ±5%, in some embodiments +1%, in some embodiments ±0.5%, and in some embodiments +0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A device for localized measurement of radiotracers in a blood vessel of interest, the device comprising a cannula sized and configured for insertion into the blood vessel of interest, and further comprising:

a measurement chamber of known volume;

an opening proximate a distal end of the cannula;

a plunger sized and configured for introducing a negative pressure in the measurement chamber when retracted for withdrawing fluid from the blood vessel of interest through the opening into the measurement chamber; and a radiation detector positioned proximate the measurement chamber-for detecting radiation emitted from the fluid withdrawn into the measurement chamber.

2. The device of claim 1 wherein the radiation detector comprises scintillation material that emits light when impacted with particles emitted from a radioactive material, wherein at least a portion of the light is received by an optical connector.

3. The device of claim 2, wherein the cannula further comprises a fiber optic material.

4. The device of claim 3, wherein the at least a portion of the light propagates via the fiber optic material to the optical connector.

5. The device of claim 3, wherein the scintillation material is shaped to focus light to at least one of the fiber optic material and the optical connector.

6. The device of claim 2, wherein the optical connector comprises an optical detector, and further wherein the optical detector converts the received light into an electrical signal for processing.

7. The device of claim 1, wherein the cannula comprises needle material.

8. The device of claim 7 wherein the needle material is operatively removable from the cannula after the cannula is positioned within the blood vessel of interest.

9. The device of claim 1, wherein the plunger is translated to re-insert the withdrawn fluid to the blood vessel of interest.

10. The device of claim 1 further comprising a particle absorption material substantially surrounding the measurement chamber and the radiation detector for shielding the radiation detector from radiation emitted from sources outside the measurement chamber.

11. The device of claim 10 wherein the particle absorption material comprises a metal.

12. The device of claim 1 wherein the radiation detector extends about a full circumference of the measurement chamber.

13. A method of measuring levels of radiotracers in a blood vessel of interest, the method comprising;

a. inserting a cannula into a blood vessel of interest, wherein the cannula comprises a measurement chamber of known volume, an opening proximate a distal end of the cannula, and a plunger sized and configured for introducing a negative pressure in the measurement chamber when retracted for withdrawing fluid from the blood vessel of interest through the opening into the measurement chamber;

b. retracting the plunger to introduce the negative pressure in the measurement chamber such that fluid from the blood vessel of interest is withdrawn into the measurement chamber; and c. utilizing a radiation detector, measuring radiation emitted from the within the measurement chamber.

14. The method of claim 13 wherein the radiation detector comprises scintillation material that emits light when impacted with particles emitted from a radioactive material, and the measurement of radiation emitted from fluid within the measurement chamber is determined using the emitted light.

15. The method of claim 14 wherein at least a portion of the emitted light is transmitted from the radiation detector via a fiber optic material to an optical detector for converting the received light into an electrical signal for processing.

16. The method of claim 13 wherein the cannula comprises needle material.

17. The method of claim 16 wherein the needle material is operatively removable from the cannula after the cannula is positioned within the blood vessel of interest.

18. The method of claim 13 wherein a particle absorption material substantially surrounds the measurement chamber and the radiation detector to shield the radiation detector from radiation emitted from sources outside the measurement chamber.

19. The method of claim 13 further comprising unretracting the plunger to remove the negative pressure in the measurement chamber such that the withdrawn fluid is returned to the blood vessel of interest.

* * * * *